(12) United States Patent
Joudrey et al.

(10) Patent No.: US 10,232,287 B2
(45) Date of Patent: Mar. 19, 2019

(54) CORROSION PROTECTION IN TUBING USED CHROMATOGRAPHY

(71) Applicant: Waters Technologies Corporation, Milford, MA (US)

(72) Inventors: Kurt D. Joudrey, Chelmsford, MA (US); Steven D. Trudeau, Webster, MA (US); Paul Keenan, Harrisville, RI (US); Joseph A. Luongo, Walpole, MA (US); Daniel J. McCormick, Westford, MA (US); Eugene Berthiaume, Cumberland, RI (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 779 days.

(21) Appl. No.: 14/382,900

(22) PCT Filed: Mar. 4, 2013

(86) PCT No.: PCT/US2013/028798
§ 371 (c)(1),
(2) Date: Sep. 4, 2014

(87) PCT Pub. No.: WO2013/134087
PCT Pub. Date: Sep. 12, 2013

(65) Prior Publication Data
US 2015/0048015 A1 Feb. 19, 2015

Related U.S. Application Data

(60) Provisional application No. 61/606,525, filed on Mar. 5, 2012.

(51) Int. Cl.
*B01D 15/08* (2006.01)
*B01D 15/22* (2006.01)
(Continued)

(52) U.S. Cl.
CPC ............. *B01D 15/22* (2013.01); *B01D 15/08* (2013.01); *B01D 15/40* (2013.01); *G01N 30/02* (2013.01);
(Continued)

(58) Field of Classification Search
CPC ...... B01D 15/22; B01D 15/206; B01D 15/08; B01D 15/40; G01N 30/52; G01N 30/6047;
(Continued)

(56) References Cited

U.S. PATENT DOCUMENTS 3,866,308 A * 2/1975 Halasz ............... G01N 30/6052
210/198.2
4,070,285 A * 1/1978 Abrahams .............. B01D 15/22
210/198.2
(Continued)

FOREIGN PATENT DOCUMENTS

EP 0053768 A2 6/1982
EP 0328146 A2 8/1989
(Continued)

OTHER PUBLICATIONS

AMP Incorporated, "Golden Rules: Guidelines for the use of gold on connector contacts". Tyco Electronics Corporation. 2004.*
(Continued)

*Primary Examiner* — Katherine Zalasky
*Assistant Examiner* — Benjamin L Lebron
(74) *Attorney, Agent, or Firm* — Schmeiser, Olsen & Watts LLP

(57) ABSTRACT

An apparatus for use in a liquid chromatography system includes a chromatography port and a tubing assembly having a chromatography tube coupled at one end to the chromatography port. The end of the tube has an end face covered with a corrosion-resistant material, for example,
(Continued)

gold. The corrosion-resistant nature of the material protects the end of the tube from corrosion or erosion, which improves the quality and reliability of a seal between the end face of the tube and a sealing surface of the port. Alternatively, or in addition to covering the end face of the tube with the corrosion-resistant material, a gasket covered with or made of the corrosion-resistant material can be disposed between the end face of the tube and the port. This gasket extends the reach of the tube to facilitate bottoming out the tube within the port.

16 Claims, 5 Drawing Sheets

(51) Int. Cl.
    *B01D 15/40*     (2006.01)
    *G01N 30/02*     (2006.01)
    *G01N 30/56*     (2006.01)
    *G01N 30/60*     (2006.01)

(52) U.S. Cl.
    CPC ............ *G01N 30/56* (2013.01); *G01N 30/60* (2013.01); *G01N 30/6026* (2013.01); *G01N 30/6004* (2013.01); *G01N 2030/027* (2013.01); *G01N 2030/6013* (2013.01)

(58) Field of Classification Search
    CPC ............ G01N 30/6052; G01N 30/60; G01N 30/6026; G01N 30/6004; G01N 30/6017; G01N 30/603; G01N 30/24; G01N 2030/027; G01N 2030/528; G01N 30/02; G01N 30/56; G01N 2030/6013; B01J 20/3236; B01J 2220/82; B01J 2220/86
    See application file for complete search history.

(56) References Cited

U.S. PATENT DOCUMENTS

| | | | | |
|---|---|---|---|---|
| 4,175,037 A | * | 11/1979 | Benney | B01D 15/206 |
| | | | | 141/12 |
| 4,451,363 A | * | 5/1984 | Brownlee | B01D 15/22 |
| | | | | 210/198.2 |
| 4,524,996 A | | 6/1985 | Hunt | |
| 4,587,014 A | * | 5/1986 | America | G01N 30/6004 |
| | | | | 210/198.2 |
| 4,751,004 A | | 6/1988 | Stevens et al. | |
| 4,863,592 A | * | 9/1989 | Allington | B01D 15/08 |
| | | | | 210/198.2 |
| 5,091,092 A | * | 2/1992 | Newhouse | G01N 30/24 |
| | | | | 210/198.2 |
| 6,086,767 A | * | 7/2000 | Walters | B01D 11/0203 |
| | | | | 210/198.2 |
| 6,162,362 A | * | 12/2000 | Ma | B01D 15/22 |
| | | | | 210/198.2 |
| 7,909,367 B2 | * | 3/2011 | Plant | G01N 30/6034 |
| | | | | 285/249 |
| 8,006,367 B1 | * | 8/2011 | Best | B01L 3/563 |
| | | | | 29/516 |
| 2004/0236083 A1 | | 11/2004 | Libert et al. | |
| 2006/0151998 A1 | * | 7/2006 | Dourdeville | F16L 13/103 |
| | | | | 285/285.1 |
| 2008/0283458 A1 | | 11/2008 | Ishii et al. | |
| 2012/0024411 A1 | * | 2/2012 | Hahn | B01D 15/22 |
| | | | | 138/109 |

FOREIGN PATENT DOCUMENTS

| | | |
|---|---|---|
| FR | 2960643 A1 | 12/2011 |
| GB | 2482175 A | 1/2012 |
| JP | 51134190 A | 11/1976 |
| JP | 62115175 U | 7/1987 |
| JP | 01224661 A | 9/1989 |
| JP | 0666777 A | 3/1994 |
| JP | 2006086124 | 3/2006 |
| JP | 2008286783 A | 11/2008 |

OTHER PUBLICATIONS

Extended European Search Report in counterpart European patent application No. 13727973.6, dated Oct. 1, 2015; 6 pg.
Notice of Rejection in counterpart Japanese patent application No. 2014-560986, dated Oct. 25, 2017; 7 pages.
International Preliminary Report on Patentability in counterpart international patent application No. PCT/US13/28798, dated Sep. 18, 2014; 7 pages.
International Search Report & Written Opinion in international patent application No. PCT/US13/28798, dated May 7, 2013; 8 pages.
O'Leary, Karey, "Enviornmental Sampling & Monitoring Primer: Supercritical Fluid Chromatography (SFC)", Copyright 1997, accessed Feb. 2, 2012; 5 pages.

* cited by examiner

CORROSION PROTECTION IN TUBING USED CHROMATOGRAPHY

RELATED APPLICATION

This application claims the benefit of and priority to U.S. provisional application No. 61/606,525, filed Mar. 5, 2012, titled "Corrosion Protection in Tubing Used in Chromatography," the entirety of which application is incorporated by reference herein.

FIELD OF THE INVENTION

The invention relates generally to liquid chromatography systems. More specifically, the invention relates to tubing treatments for protection from corrosion in chromatography systems.

BACKGROUND

Chromatography is a set of techniques for separating a mixture into its constituents. Well-established separation technologies include HPLC (High Performance Liquid Chromatography), UPLC (Ultra Performance Liquid Chromatography), and SFC (Supercritical Fluid Chromatography). HPLC systems use high pressure, ranging traditionally between 1,000 psi (pounds per square inch) to approximately 6,000 psi, to generate the flow required for liquid chromatography in packed columns. In contrast to HPLC, UPLC systems use columns with smaller particulate matter and higher pressures approaching 20,000 psi to deliver the mobile phase. SFC systems use highly compressible mobile phases, which typically employ carbon dioxide ($CO_2$) as a principle component.

In general, in a liquid chromatography (LC) application, a solvent delivery system takes in and delivers a mixture of liquid solvents to an autosampler (also called an injection system or sample manager), where an injected sample awaits the arrival of this mobile phase. The mobile phase carries the sample through a separating column. In the column, the mixture of the sample and mobile phase divides into bands depending upon the interaction of the mixture with the stationary phase in the column. A detector identifies and quantifies these bands as they exit the column.

Tubing between equipment used in liquid chromatography, such as valves, pumps, and the column is typically made of stainless steel. Such material is readily available and capable of handling the elevated pressures and temperature range required for chromatography. Despite its hardiness, however, this material may corrode or erode at connection points to the detriment of the chromatographic results. The effects of the corrosion or erosion may include the loss of pressure or of flow, which affect retention times. Other negative effects may include carryover, and tailing and fronting of peaks.

SUMMARY

In one aspect, the invention features an apparatus comprising a chromatography port and a tubing assembly having a chromatography tube with a bore extending therethrough. The chromatography tube is coupled at one end to the chromatography port. The one end of the chromatography tube has an end face covered with a corrosion-resistant material.

In another aspect, the invention features an apparatus comprising a chromatography port and chromatography tubing coupled at one end to the chromatography port. The end of the chromatography tubing has an end face. The apparatus further comprises a gasket disposed between the end of the chromatography tubing and the chromatography port. One side of the gasket abuts the end face of the chromatography tubing and the opposite side of the gasket abuts a sealing surface of the chromatography port. The gasket is covered with or made of corrosion-resistant material.

In still yet another aspect, the invention features a tubing assembly comprising a chromatography tube with a bore extending from one end of the tube to an opposite end of the tube. One of the ends of the tube has an end face covered with a corrosion-resistant material.

In another aspect still, the invention features a liquid chromatography system comprising a component with a chromatography port and a tubing assembly with a chromatography tube having a bore extending therethrough. The chromatography tube is coupled at one end to the chromatography port with the bore of the chromatography tube axially aligned with the fluidic channel at the chromatography port. The end of the chromatography tube has an end face covered with a corrosion-resistant material.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Applicant recognized that erosion or corrosion of tubing used in a liquid chromatography system can lead to sample carryover, peak fronting and tailing, or pressure loss, which are phenomena known to affect negatively the chromatography results. Such erosion or corrosion is thought to occur primarily at the joints where the tubing connects to a component of the liquid chromatography system, such as an injector valve or a column, although corrosion of the tubing can conceivably occur anywhere along its length.

To minimize or eliminate the erosion or corrosion at connection points, portions of the ports and/or tubes are covered (i.e., coated, plated, or treated) with a malleable, corrosion-resistant relatively chemically inert material, one that can withstand the temperature and pressure requirements of liquid chromatography systems. Herein, the terms coated, plated, and treated (and variations thereof) are interchangeably used, without any implicit limiting of the principles described herein to the particular process used to produce the layer of corrosion-resistant material on the tube. Preferably, the plating covers the end face at one or both ends of the tube. In addition, the plating can extend to the inside surface of the tube, preferably for the entire tube's length, or as far into the tube as the plating process and the inner diameter (ID) of the tube will allow. In addition, the facing surface of the ports that contact the tubes can be plated with the corrosion-resistant material. For those connection joints where the thickness of the plating on the end face of the tubing may not be sufficient for the tube to "bottom out" in a port, a gasket coated with or made of the corrosion-resistant material can be placed at the tube end, in effect, extending the tube to make contact with a sealing surface of the port. This gasket can be bonded to the end face of the tube or placed separately within the port before insertion of the tube.

In one embodiment, the corrosion-resistant material is gold (either hard gold or soft gold). Gold is useful in this application because of its high ductility, malleability, resistance to corrosion, and relative chemical inertness. An example of another corrosion-resistant, relatively chemically inert material for use in covering the tubing is tantalum. Another example is platinum.

Figure 1:
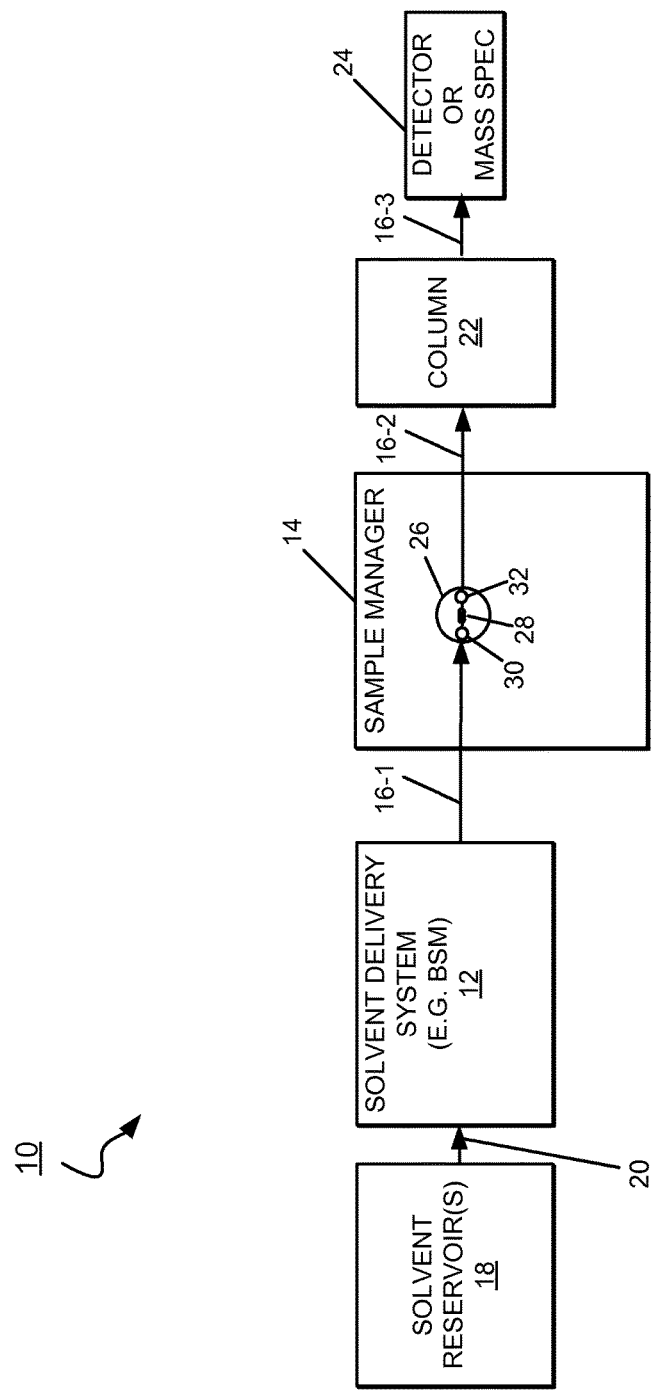
FIG. 1 is a functional block diagram of an embodiment of a liquid chromatography system.

FIG. 1 shows an embodiment of a liquid chromatography system 10 for separating a sample into its constituents. The liquid chromatography system 10 can be, for example, an HPLC, UPLC, or a $CO_2$-based system. In brief overview, the liquid chromatography system 10 includes a solvent delivery system 12 in fluidic communication with a sample manager 14 (also called an injector or autosampler) through tubing 16-1. The solvent delivery system 12 includes pumps (not shown) in fluidic communication with solvent (or fluid) reservoirs 18 from which the pumps draw solvents through tubing 20. A chromatography column 22 is in fluidic communication with the sample manager 14 through tubing 16-2. Tubing 16-3 couples the output port of the column 22 to a detector 24, for example, a mass spectrometer. Through the tubing, the detector 24 receives the separated components from the column 22 and produces an output from which the identity and quantity of the analytes may be determined. As described herein, the tubing 16-1, 16-2, 16-3 (generally, 16) are partially or fully covered with a corrosion-resistant material, used in conjunction with a plated end-face gasket, or both. Each tubing 16 refers generally to a section of tubing rather than to a single tube; each tubing section may comprise one tube or multiple tubes (e.g., by valves, tees, etc).

The sample manager 14 includes an injector valve 26 with a sample loop 28. In one embodiment, the injector valve is a rotary shear valve. The solvent manager 14 operates in one of two states: a load state and an injection state. In the load state, the position of the injector valve 26 is such that the solvent manager 14 loads the sample into the sample loop 28; in the injection state, the position of the injector valve 26 changes so that solvent manager 14 introduces the sample in the sample loop 28 into the continuously flowing mobile phase arriving from the solvent delivery system 12. With the injector valve 26 in the injection state, the mobile phase carries the sample into the column 22, the mobile phase arriving at the injector valve 26 through an input port 30 and leaving with the sample through an output port 32.

The various connection joints benefiting from the treated tubing, ports, and/or gasket include, but are not limited to, where the tubing 16-1 connects to the input port 30 of the injector valve 26, where the tubing 16-2 connects to the output port 32 of the injector valve 26 and to the column 22, and where the tubing 16-3 connects to the output end of the column 22 and to the detector 24.

Figure 2:
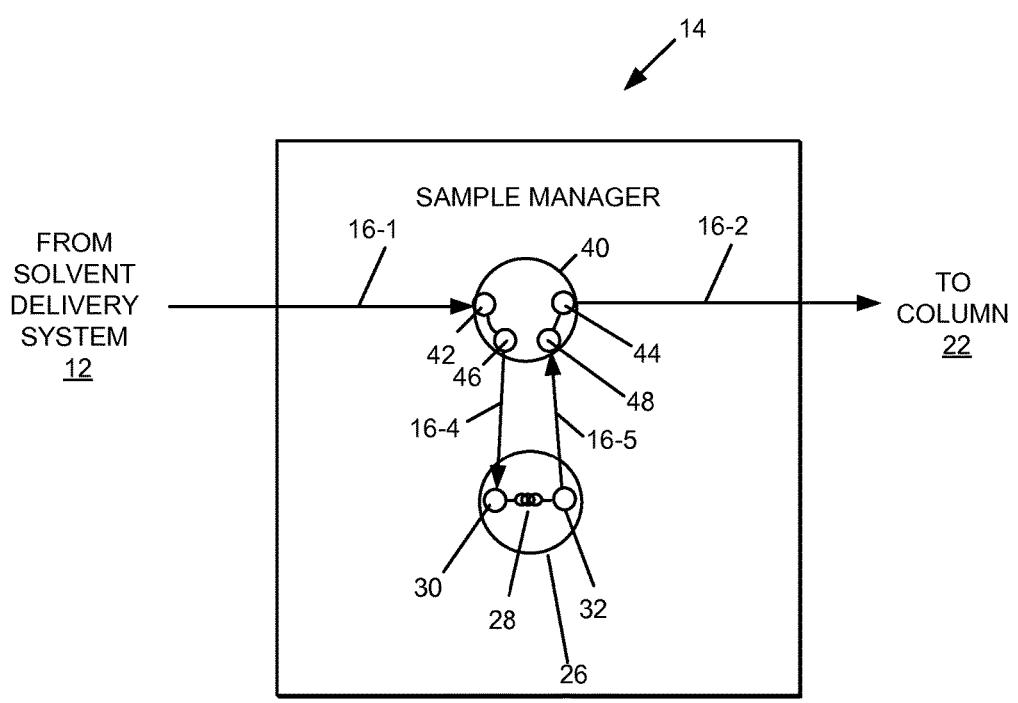
FIG. 2 is a functional diagram of an embodiment of a solvent manager of a liquid chromatography system.

As shown in FIG. 2, in some embodiments, for example, those in which the liquid chromatography system 10 employs a $CO_2$-based mobile phase, the sample manager 14 can further include an auxiliary valve 40 interposed between the solvent delivery system 12 and the injector valve 26 and between the injector valve 26 and the column 22. Although shown to be part of the sample manager 14, the auxiliary valve 40 can be implemented in another piece of equipment remote to the injector valve 26. Like the injector valve 26, the auxiliary valve 40 can be implemented using a rotary shear valve. In general, the auxiliary valve 40 provides a fluidic pathway through which the injector valve 26 may vent. In this embodiment, the tubing 16-1 couples the solvent delivery system 12 to an input port 42 of the auxiliary valve 40 and the tubing 16-2 couples an output port 44 of the auxiliary valve 40 to the column 22. Tubing 16-4 and 16-5 couples the auxiliary valve 40 to the injector valve 26; tubing 16-4 connects port 46 of the auxiliary valve 40 to the input port 30 of the injector valve 26, and tubing connects port 48 of the auxiliary valve 40 to the output port 32 of the injector valve 26.

When the valves 26, 40 are configured for sample injection, the arrows on the tubing 16-1 and 16-4 show the direction of flow of the mobile phase towards the injector valve 26; those arrows on the tubing 16-5 and 16-2 correspond to the flow of the mobile phase carrying the sample from the injector valve 26 towards the column 22.

Like the tubing 16 described in connection with FIG. 1, the tubing 16-4 and 16-5 are also partially or fully treated with a corrosion-resistant material, used in conjunction with a plated end-face gasket, a plated port, or any combination thereof. The additional connection joints benefiting from the treated tubing and/or end-face gasket include where the tubing 16-4 connects to the input port 30 of the injector valve 26 and to the port 46 of the auxiliary valve 40, and where the tubing 16-5 connects to the output port 32 of the injector valve 26 and to the port 48 of the auxiliary valve 40.

Figure 3:
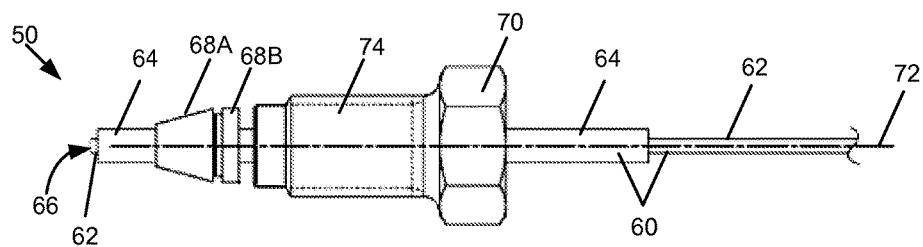
FIG. 3 is a side view of an embodiment of a fitting for joining fluidic pathways, the fitting comprising a tubing assembly, the tubing assembly comprising a tube, a portion of which is coated with a corrosion-resistant material.

FIG. 3 shows an embodiment of a fitting 50 for coupling two fluidic paths, for example, to couple the tubing 16-1, 16-2 of FIG. 1 or the tubing 16-4, 16-5 of FIG. 2 to a port of a rotary shear seal valve. The fitting 50 includes a tube assembly 60 having a tube 62 surrounded by a sleeve 64. Either or both the tube 62 and the sleeve 64 can be made of stainless steel. Materials other than stainless steel can be used for the tube 62 and the sleeve 64. A weld may join the tube 62 to the sleeve 64. As an example, the inner diameter (ID) and outer diameter (OD) of the tube 62 can be 0.007 in. and 0.025 in., respectively, and the outer diameter of the sleeve 64 can be 0.062 in. The end face 66 of the tube 62 is substantially normal to the longitudinal axis 72 of the tube 62 and has a low surface roughness. A portion of the tube 62 protrudes from the end of the sleeve 64. The length of the protrusion allows the end face 66 of the tube 62 to contact a sealing surface of a port (e.g., of the injector valve 26), which may also be covered with a corrosion-resistant material.

In general, any portion of the tube 62, its end faces, inner surface, and outer surface, and the sleeve 64 can be plated with the corrosion-resistant material. Use of the term "plating" or "plated" in connection with the tube is not intended to limit the principles described herein to the particular process used to produce the layer of corrosion-resistant material on the tube. It is to be understood that any one of various conventional processes, including, for example, electroplating and vapor deposition, can be used to cover, coat, treat, or plate the tube, partially or fully, without departing from the principles described herein.

Preferably, at least the end face 66 is plated. In addition, the plating of the corrosion-resistant material can extend to the inside of the tube 62 to a depth of approximately equal to or greater than the inner diameter (ID) of the tube. For example, for a tube with a 0.007-inch ID, the plating of the corrosion-resistant material extends at least 0.007 inches into the tube 62. Preferably, a plating thickness in the range of 2-4 µm is generally thick enough to achieve corrosion resistance and to fill any surface imperfections on the end face 66 of the tube 62 and on the sealing surface of the port. Plating thicknesses that far exceed this range can produce a "gasket" between the end face 66 of the tube 62 and the sealing surface of the mating port. This gasket can serve to span any gap between the end face 66 of the tube 62 and the sealing surface of the port.

The fitting 50 further includes a two-part compression member 68A, 68B (generally 68) and a compression screw 70, each of which encircle the tube assembly 60. The two-part compression member 68 has a front-coned portion 68A and a back ring 68B. The compression member 68 can be, for example, a stainless steel ferrule set (e.g., part no. SS-100-SET available from Swagelok Company of Solon, Ohio). The compression screw 70 has threads 74 for engaging threads of the receiving port.

Figure 4:
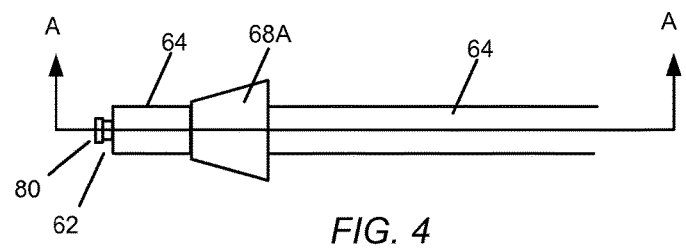
FIG. 4 is a side view of the tubing assembly and a compression member coupled to the tubing assembly, the tubing assembly including a tube having a gasket at one end, the gasket being coated with or made of a corrosion-resistant material.
Figure 5:
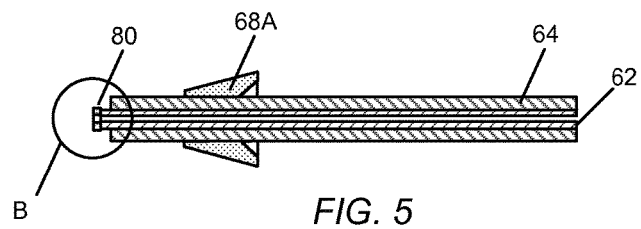
FIG. 5 is a cross-section view of the tubing assembly.

FIG. 4 shows the fitting 50 of FIG. 3 without the back ring 68B of the two-part compression member 68A, 68B and without the compression screw 70, and FIG. 5 shows a cross-section of the fitting 50 along the line A-A in FIG. 4. In addition, the tube assembly 60 here includes a washer 80 plated with or made of a corrosion-resistant material and attached to the end face 66 (FIG. 3) of the tube 62. Plating limitations might not allow for a thick enough plating layer to produce a gasket on the end face of the tube 62. Accordingly, this washer 80 provides that gasket. The washer (hereafter, gasket 80) can be used instead of or in addition to plating the end face 66 (and/or the inner surface) of the tube 62.

Known techniques, for example, laser weld, e-beam weld, and thermal compression bonding, can join the gasket 80 to the end face 66 of the tube 62. A purpose for joining the gasket 80 to the end face 66 is to prevent the gasket 80 from becoming stuck in the bottom of the receiving port (e.g., upon removal of the fitting 50).

Figure 6:
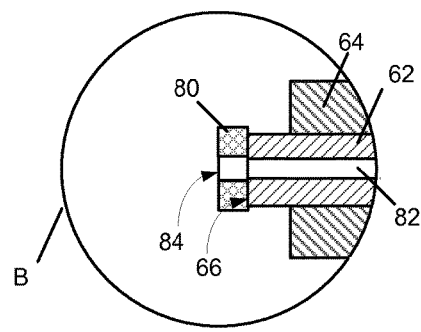
FIG. 6 is a detail view of the end of the tubing assembly with the gasket coated or made of a corrosion-resistant material.

FIG. 6 shows a detail view corresponding to the circle B in FIG. 5. The detail view shows the placement of gasket 80 on the end face 66 of the tube 62. The bore 82 of the tube 62 aligns with the central opening 84 in the gasket 80. The inner diameter of the gasket 80 is approximately equal to or slightly greater than the inner diameter of the tube 62, and the outer diameter of the gasket 80 is optionally greater than the outer diameter of the tube 62. In one embodiment, the thickness of the gasket 80 is 0.010 in.

Figure 7:
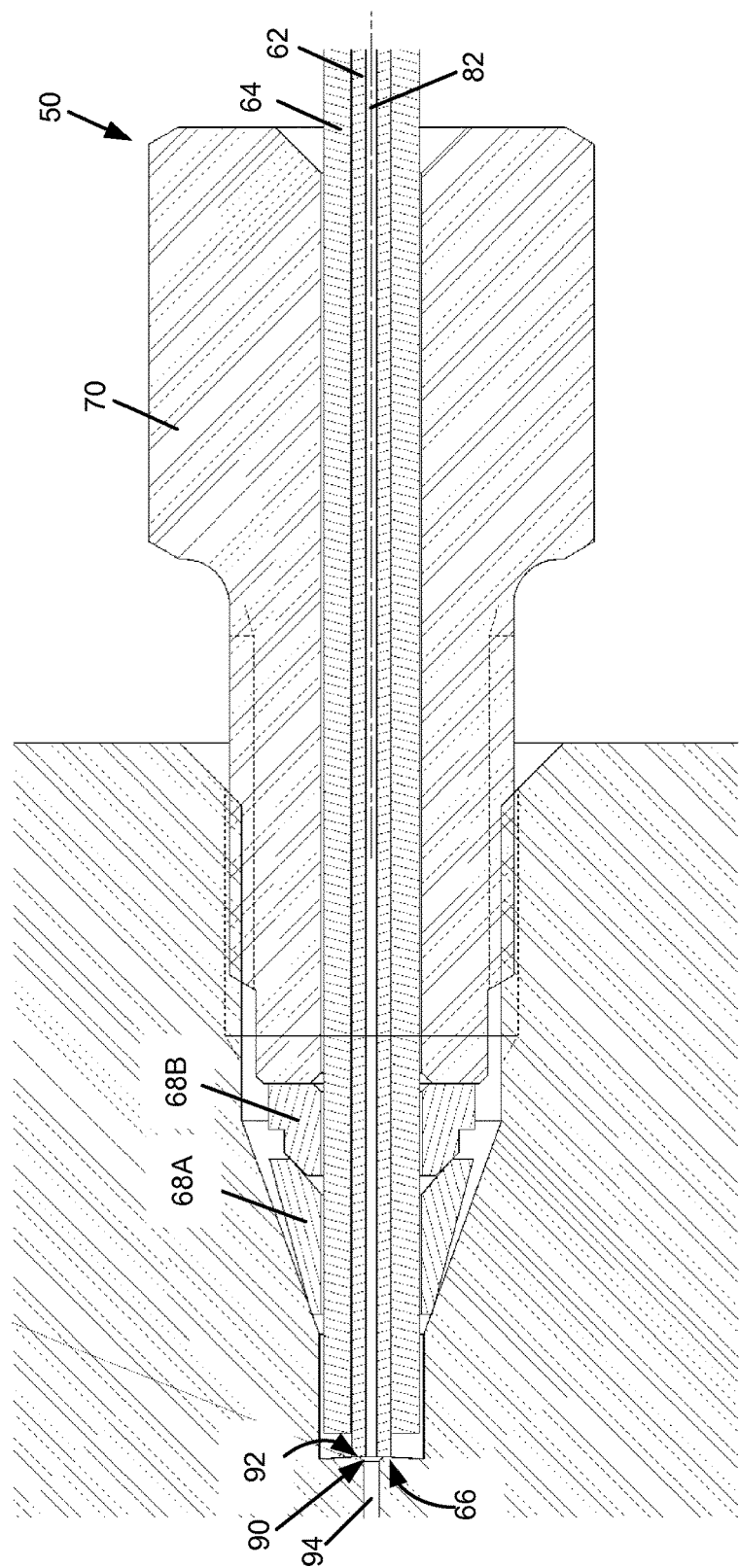
FIG. 7 is a cross-section view of the fitting of FIG. 2 installed within a port.

FIG. 7 shows the fitting 50 mated with a port 90, the tube assembly 60 and the two-part compression member 68A, 68B being disposed within a cavity of the receiving port 90. When securing the fitting 50 to the port, the user tightens the compression screw 70, which causes the compression member 68A, 68B to grip the sleeve 64 and urges the end face 66 of the tube 62 towards the sealing surface 92 of the port 90. In this example, the end face 66 physically contacts the sealing surface 92 (i.e., "bottoms out"), with the bore 82 of the tube 62 aligning with the fluidic channel 94 at the bottom of the port 90. With the compression screw 70 adequately tightened, the end face 66 of the tube 62 produces a fluid-tight seal against the sealing surface 92 of the port 90. Because the end face 66 and, optionally, a portion of the inner surface of the tube 62 are plated with a malleable, corrosion-resistant relatively chemically inert material, the quality and reliability of the fluid-tight seal is improved by filling the surface imperfections on the end face 66 and on the sealing surface 92 and by resisting corrosion and erosion at the tube's end.

Figure 8:
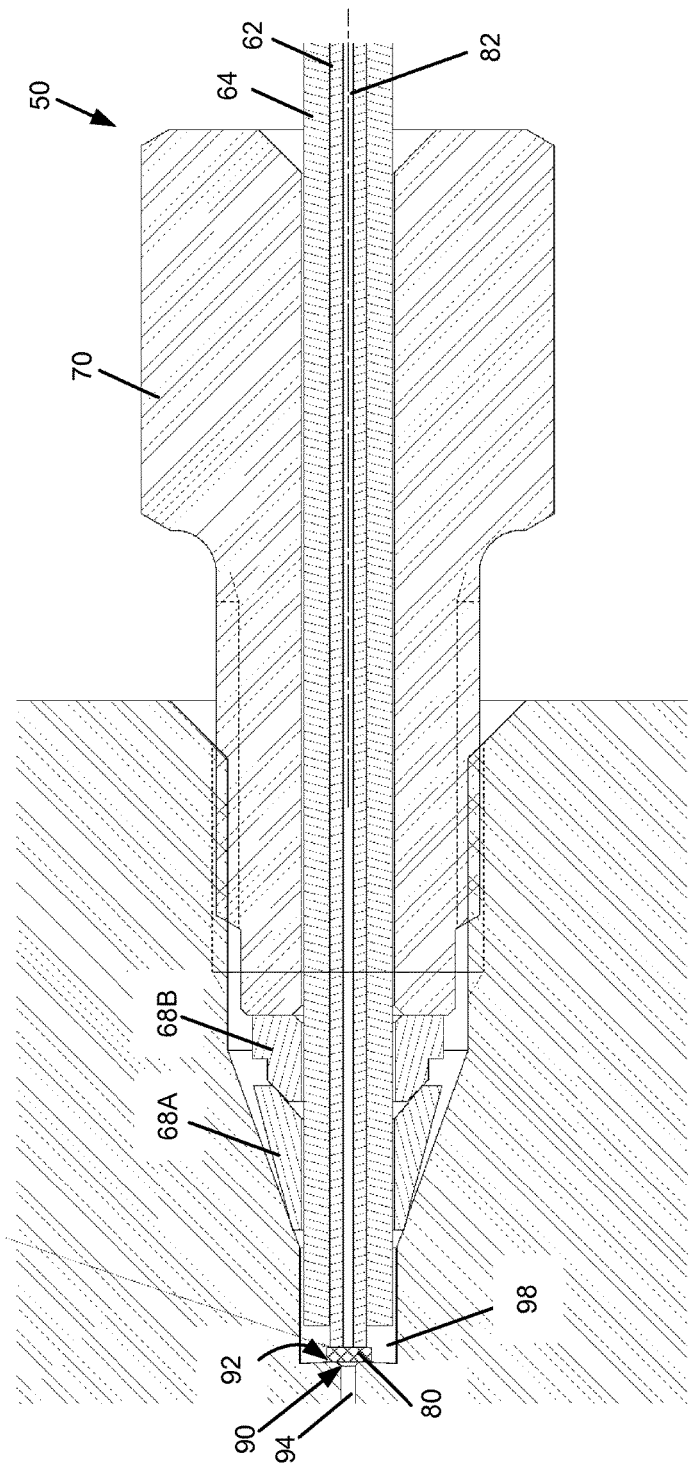
FIG. 8 is cross-section view of the fitting installed within a port, the fitting having a tubing assembly comprising a tube with a gasket at one end, the gasket being coated with or made of a corrosion-resistant material.

FIG. 8 shows another example of the fitting 50 mated with the port 90. In this example, the compression screw 70 and the two-part compression member 68A, 68B seal the joint between the two fluidic pathways 82, 94 before the end face 66 of the tube can physically contact the sealing surface 92 of the port 90. The tube 62 does not bottom out. In this instance, the chromatography results could be subjected to carryover because sample or analytes can fill the sealed cavity 98. As shown, use of the gasket 80, plated with or constructed of malleable, corrosion-resistant, relatively chemically inert material, spans the distance between the end face 66 and the sealing surface 92 of the port 90, and produces a fluid-tight, imperfection-filling, corrosion-resistant seal against the sealing surface 92. The gasket 80 couples the bore 82 of the tube 62 directly to the fluidic channel 94 of the port 90. Consequently, sample or analytes cannot spill into the cavity 98, where they could subsequently contribute to carryover.

Reference in the specification to "one embodiment" or "an embodiment" means that a particular, feature, structure or characteristic described in connection with the embodiment is included in at least one embodiment of the teaching. References to a particular embodiment within the specification do not all necessarily refer to the same embodiment.

While the invention has been shown and described with reference to specific preferred embodiments, it should be understood by those skilled in the art that various changes in form and detail may be made therein without departing from the spirit and scope of the invention as defined by the following claims.

What is claimed is:
1. A liquid chromatography system, comprising:
 a component with a chromatography port to a fluidic channel; and
 a tubing assembly with a chromatography tube surrounded by a sleeve, the chromatography tube having an inner surface defining a bore extending therethrough and an outer surface, the chromatography tube being coupled at one end to the chromatography port with the bore of the chromatography tube axially aligned with the fluidic channel at the chromatography port, the one end of the chromatography tube having an end face covered with a corrosion-resistant material, wherein a portion of the inner surface near the end face protrudes from an end of the sleeve and is also covered with the corrosion-resistant material.

2. The liquid chromatography system of claim 1, further comprising a gasket attached to the end face of the chromatography tube, the gasket abutting a surface of the chromatography port, the gasket being covered with the corrosion-resistant material.

3. The liquid chromatography system of claim 1, wherein the corrosion-resistant material comprises gold.

4. The liquid chromatography system of claim 1, wherein the component is at least one of: a chromatography column; an injector valve; and an auxiliary valve.

5. The liquid chromatography system of claim 1, wherein the chromatography tube is made of stainless steel.

6. The liquid chromatography system of claim 1, wherein a sealing surface of the chromatography port is covered with a corrosion-resistant material.

7. The liquid chromatography system of claim 1, wherein at least a portion of the outer surface adjacent the end face of the chromatography tube is covered with the corrosion-resistant material.

8. The liquid chromatography system of claim 1, wherein the corrosion-resistant material extends at least one of: from the end face of the chromatography tube to an inside of the chromatography tube; inside of the chromatography tube to a depth equal to or greater than an inner diameter of the chromatography tube; and inside of the chromatography tube at least 0.007 inches.

9. The liquid chromatography system of claim 1, wherein the corrosion-resistant material has a thickness of about two micrometers to about four micrometers.

10. The liquid chromatography system of claim 2, wherein the gasket is separated from the sleeve by the end face.

11. The liquid chromatography system of claim 2, wherein an inner diameter of the gasket is greater than an inner diameter of the chromatography tube.

12. The liquid chromatography system of claim 2, wherein an outer diameter of the gasket is greater than an outer diameter of the chromatography tube.

13. The liquid chromatography system of claim 2, wherein a thickness of the gasket is about 0.010 inches.

14. The liquid chromatography system of claim 1, wherein the liquid chromatography system is a supercritical fluid chromatography system.

15. The liquid chromatography system of claim 2, wherein the gasket spans a distance between the end face of the chromatography tube and a sealing surface of the chromatography port and produces a corrosion resistant seal against the sealing surface of the chromatography port.

16. The liquid chromatography system of claim 2, wherein the gasket couples the bore of the chromatography tube to the fluidic channel at the chromatography port and prevents spillage into the cavity around the gasket.

* * * * *

UNITED STATES PATENT AND TRADEMARK OFFICE
CERTIFICATE OF CORRECTION

PATENT NO. : 10,232,287 B2
APPLICATION NO. : 14/382900
DATED : March 19, 2019
INVENTOR(S) : Kurt D. Joudrey et al.

Page 1 of 1

It is certified that error appears in the above-identified patent and that said Letters Patent is hereby corrected as shown below:

On the Title Page

In the Title:
Add the word "In" between the words "Used" and "Chromatography"

Signed and Sealed this
Eighteenth Day of June, 2019

Andrei Iancu
*Director of the United States Patent and Trademark Office*